(12) United States Patent
Jiang et al.

(10) Patent No.: US 8,574,737 B2
(45) Date of Patent: Nov. 5, 2013

(54) BIOELECTRIC BATTERY FOR IMPLANTABLE DEVICE APPLICATIONS

(75) Inventors: Naixiong Jiang, Mt. View, CA (US);
Gene A. Bornzin, Simi Valley, CA (US);
John W. Poore, South Pasadena, CA (US); Sheldon Williams, Green Valley, CA (US); Weiqun Yang, Cupertino, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/018,140

(22) Filed: Jan. 31, 2011

(65) Prior Publication Data

US 2011/0202105 A1 Aug. 18, 2011

Related U.S. Application Data

(62) Division of application No. 11/737,307, filed on Apr. 19, 2007.

(51) Int. Cl.
*H01M 4/00* (2006.01)
*H01M 8/16* (2006.01)
*H01M 4/02* (2006.01)
*H01M 2/16* (2006.01)

(52) U.S. Cl.
USPC ............ 429/94; 429/2; 429/209; 429/247

(58) Field of Classification Search
USPC .................... 429/94, 2, 209, 247
See application file for complete search history.

(56) References Cited

U.S. PATENT DOCUMENTS

| | | | | |
|---|---|---|---|---|
| 3,884,243 A | * | 5/1975 | Cywinski | 607/35 |
| 3,897,267 A | * | 7/1975 | Tseung et al. | 607/35 |
| 5,782,879 A | * | 7/1998 | Rosborough et al. | 607/6 |
| 2004/0241537 A1 | * | 12/2004 | Okuyama et al. | 429/86 |

* cited by examiner

*Primary Examiner* — Helen O Conley
(74) *Attorney, Agent, or Firm* — Theresa A. Raymer; Steven M. Mitchell

(57) ABSTRACT

A bioelectric battery may be used to power implantable devices. The bioelectric battery may have an anode electrode and a cathode electrode separated by an insulating member comprising a tube having a first end and a second end, wherein said anode is inserted into said first end of said tube and said cathode surrounds said tube such that the tube provides a support for the cathode electrode. The bioelectric battery may also have a membrane surrounding the cathode to reduce tissue encapsulation. Alternatively, an anode electrode, a cathode electrode surrounding the cathode electrode, a permeable membrane surrounding the cathode electrode. An electrolyte is disposed within the permeable membrane and a mesh surrounds the permeable membrane. In an alternative embodiment, a pacemaker housing acts as a cathode electrode for a bioelectric battery and an anode electrode is attached to the housing with an insulative adhesive.

23 Claims, 3 Drawing Sheets

BIOELECTRIC BATTERY FOR IMPLANTABLE DEVICE APPLICATIONS

PRIORITY CLAIM

This application is a Divisional application of and claims priority and other benefits from U.S. patent application Ser. No. 11/737,307, filed Apr. 19, 2007, entitled "BIOELECTRIC BATTERY FOR IMPLANTABLE DEVICE APPLICATIONS," incorporated herein by reference in its entirety.

BACKGROUND OF THE INVENTION

1. Field of the Invention

This invention relates to power sources for implantable device applications and more particularly to a bioelectric battery or biogalvanic cell.

2. Background Art

Space is a critical design element in implantable devices. In many implantable device applications, the power source occupies a large volume of the overall implantable device. Currently, many implantable devices utilize lithium batteries disposed within the implantable device as a power source. In order to minimize the size of the implantable device, it is desirable to use a power source having the greatest possible energy density. It is also desirable to utilize a power source having excellent longevity characteristics.

BRIEF SUMMARY OF THE INVENTION

Disclosed is a power source for an implantable device application and more particularly a bioelectric battery or biogalvanic cell for use as a power source for an implantable device.

In one embodiment, the implantable bioelectric battery comprises an anode electrode, a cathode electrode and an insulating member separating the anode electrode and the cathode electrode, wherein the insulating member comprises a tube having a first end and a second end and wherein the anode electrode is inserted into the first end of the tube and the cathode electrode surrounds the tube such that the tube provides a support for the cathode electrode. The implantable bioelectric battery may further comprise a membrane surrounding said cathode electrode to reduce tissue encapsulation.

In another embodiment, the implantable bioelectric battery comprises an anode electrode, a cathode electrode surrounding the anode electrode, a permeable membrane encapsulating the cathode electrode, an electrolyte disposed within the permeable membrane, and a mesh surrounding the permeable membrane.

In a third embodiment, the implantable bioelectric battery is integrated with a pacemaker or other device such that the pacemaker or other device also acts as the cathode electrode. For example, the can of a pacemaker may be used as the cathode electrode and the anode electrode may be attached to the can of the pacemaker by an insulative adhesive.

BRIEF DESCRIPTION OF THE DRAWINGS/FIGURES

DETAILED DESCRIPTION OF THE INVENTION

Figure 1:
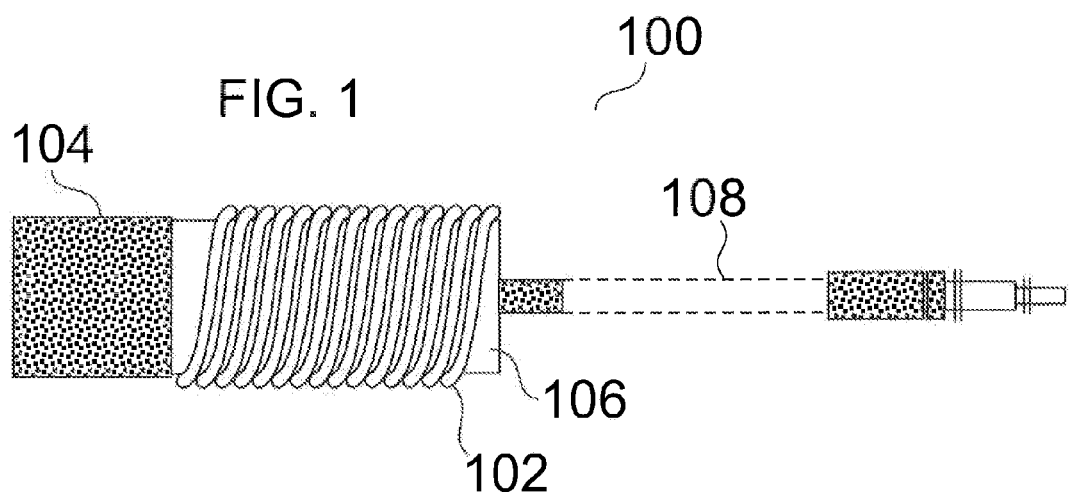
FIG. 1 is an exemplary bioelectric battery according to a first embodiment.

Disclosed herein is a bioelectric battery for implantable device applications. The bioelectric battery disclosed herein has the advantages of small size, low cost and long lifetime and can be utilized as a low power source for implanted devices. For example, the bioelectric batteries disclosed herein may provide power to an implanted device on the order of 100 μW.

Bioelectric batteries, also known as biogalvanic cells, are implanted in the body and rely on oxygen in internal body fluids for creating a voltage between an anode electrode and a cathode electrode. Oxygen in the body fluids reacts with the anode and consumes the anode, thereby creating an electric potential between the anode and cathode electrodes. Oxygen is present in the body in plentiful supply so the lifetime of the battery is limited only by the amount of anode material.

A first embodiment will be described with reference to FIGS. 1-3. A first embodiment of the bioelectric battery is generally shown at 100 in FIG. 1. Bioelectric battery 100 has a cathode electrode 102 and an anode electrode 104 built into a single unit. Cathode 102 and anode 104 are separated by an insulating member 106. Insulating member 106 is a dielectric material including, without limitation, silicone, polytetrafluoroethylene, or other dielectric polymer and may be formed in the shape of a cylindrical tube. Anode 104 may also be cylindrical in shape and inserted into a first end of insulating member 106. Cathode 102 may be in the form of a wire and is coiled around insulating member 106.

Materials are chosen for anode 104 and cathode 102 that do not exhibit toxicity to the body of the organism in which they are implanted. Anode 104 is a reactive consumable metal that is consumed during the operation of the bioelectric battery and released into the body. Therefore it should be a material that is normally present in the body and of a size that when released into the body does not increase the levels of the material beyond a normally recommended level. Anode material 104 should generate a high voltage with oxygen. The material for anode 104 may include, but is not limited to, magnesium alloys. Magnesium alloys include magnesium along with aluminum, zinc, manganese, silver, copper, nickel, zirconium and/or rare earth elements, such as neodymium, gadolinium, and yttrium. Such magnesium alloys include, without limitation, AZ61A supplied by Metal Mart International or AZ91E, EL21, or WE43 supplied by Magnesium Elektron.

The material for cathode 102 is a non-consumable metal including, without limitation, platinum or titanium. Cathode 102 may be in the form of, including, without limitation, a metal foil or wire. Cathode 102 may also have a coating that acts as a catalyst for the reaction at cathode 102. A coating increases the surface area of cathode 102, thereby resulting in a faster reaction and increased voltage generation. The coating may include, without limitation, platinum black, iridium oxide ($IrO_2$), ruthenium oxide ($RuO_2$) or an $IrO_2/RuO_2$ mixture. For example, cathode 102 may be a platinum black coated platinum wire or an iridium oxide coated titanium wire. The coating may be applied using conventional methods including, without limitation, electrochemical deposition, thermal decomposition or sputtering.

The electrolyte for the bioelectric battery 100 may be a body fluid including, without limitation, blood. When the electrolyte is a body fluid, the body fluid directly contacts cathode 102 and anode 104, such that oxygen dissolved in the body fluid is absorbed onto a surface of cathode 102 and reacts with anode 104.

A first end of a lead 108, such as pacing lead with an IS-1 connection, extends from a second end of insulating member 106 and provides a current flow between anode 104 and cathode 102 and provides power to a load 312, including, without limitation, an implantable medical device, connected to a second end of lead 108. Exemplary implantable medical devices include, without limitation, pacemakers, monitors or implantable cardioverter defibrillators (ICDs). Bioelectric battery 100 may be sufficient to power an implantable monitor; intrapericardial pacemaker, intraventricular pacemaker or standard pacemaker; or the background operations of an ICD.

In one embodiment, a magnesium alloy cylinder 104 is inserted into silicone tubing 106 and a platinum wire 102 is coiled around the silicone tubing. The magnesium alloy cylinder 104 and platinum wire 102 are connected to pacing leads 108 to act as the anode electrode and cathode electrode, respectively, of bioelectric battery 100. Magnesium and oxygen in the body fluids are slowly consumed as a current is generated. The platinum wire may be coated, such as with a platinum black coating. Alternatively, a titanium wire may be used as the cathode electrode. The titanium wire may be coated, such as with a platinum black, iridium oxide or ruthenium oxide coating.

Bioelectric battery 100 may be implanted anywhere in the body of an organism including, without limitation, subcutaneously in the neck, the pectoral cavity, the superior vena cava, the intrapericardial space or the peritoneal cavity. Bioelectric battery 100 is implanted in tissue or blood vessels such that cathode 102 and anode 104 are in direct contact with body fluids. Therefore, the body fluids act as the electrolyte for bioelectric battery 100.

Figure 2:
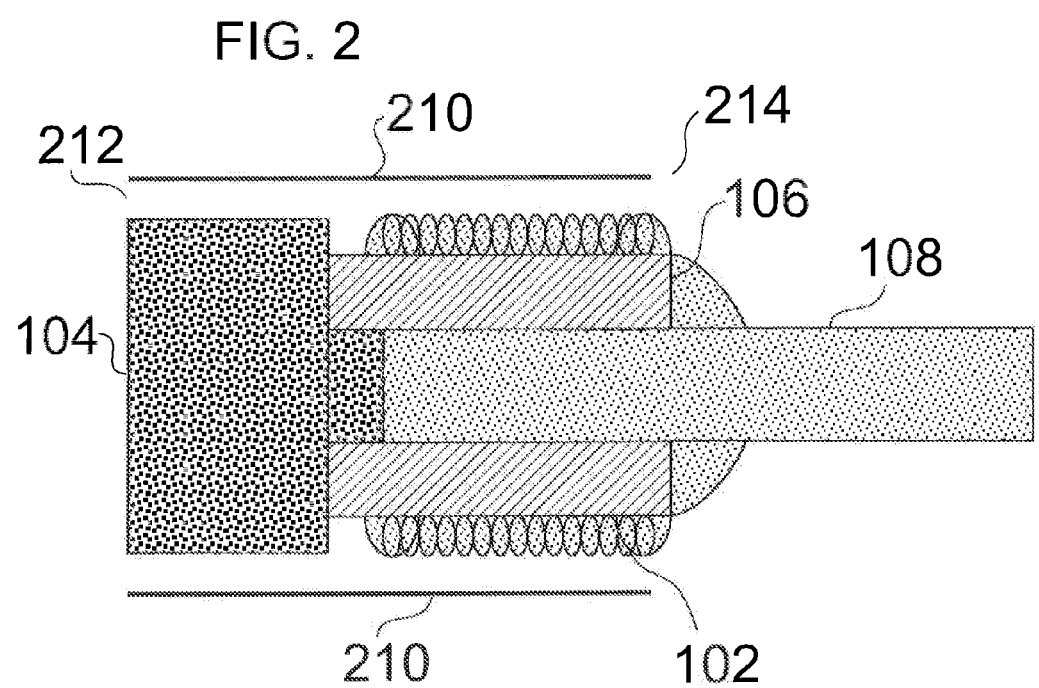
FIG. 2 is a cross-sectional view of an exemplary bioelectric battery according to a first embodiment.

As shown in FIG. 2, bioelectric battery 100 may have a membrane 210 surrounding anode 104 and cathode 102. Membrane 210 is wrapped around anode 104 and cathode 102, or may be wrapped around only cathode 102. The wrapped membrane 210 has a first open end 212 and a second open end 214 through which body fluid may flow such that body fluid contacts anode 104 and cathode 102. Implanted bioelectric batteries may have problems with tissue growing over the battery, a phenomenon known as tissue encapsulation. Tissue encapsulation occurs when body tissue grows over an electrode, reducing the amount of oxygen contacting the surface of the electrode and therefore, decreasing the efficiency of the battery. Membrane 210 is made of a material that minimizes tissue encapsulation including, without limitation, silicone. Material for membrane 210 is also porous and permeable to oxygen.

Bioelectric battery 100 may have different sizes depending upon where it will be implanted in the body. For example, a battery that is 10 mm in diameter and 50 mm in length can be utilized when the battery is to be implanted in the intrapericardial space or abdomen. Also for example, a battery that is 5 mm in diameter and 55 mm in length can be utilized when the battery is to be implanted in smaller areas such as the superior vena cava (SVC). These dimensions are merely exemplary and bioelectric battery 100 is not limited to these dimensions. Other exemplary dimensions include, but are not limited to, 5 mm in diameter and 48 mm in length; 5 mm in diameter and 50 mm in length; or 10 mm in diameter and 43 mm in length.

Figure 3:
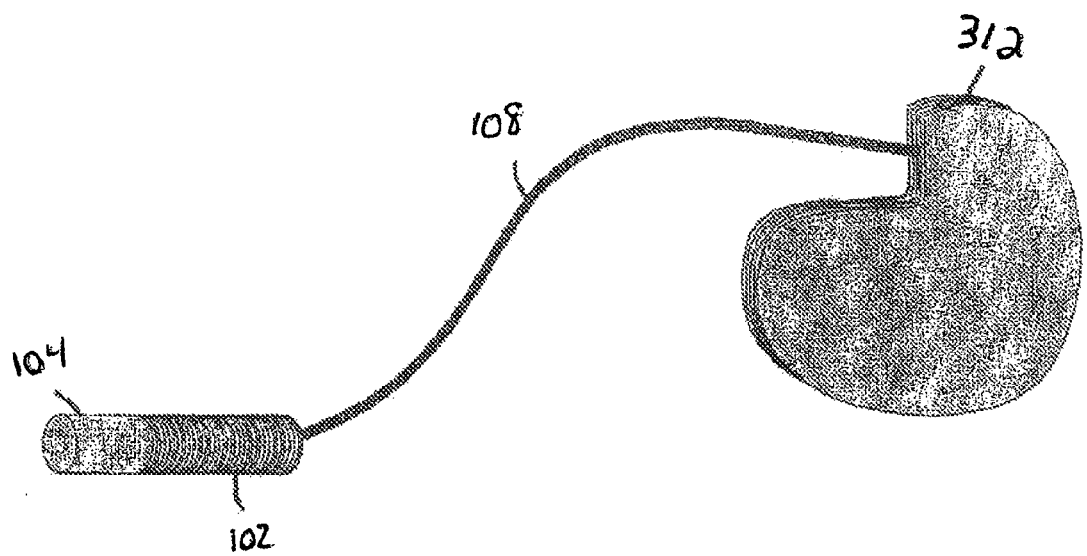
FIG. 3 is an exemplary view of an exemplary bioelectric battery according to a first embodiment connected to an exemplary medical device.

While FIGS. 1-3, show bioelectric battery 100 as a single unit, anode 104 and cathode 102 may be separated, for example, anode 104 may be implanted a predetermined distance from cathode 102 that allows for an electric potential to exist between cathode 102 and anode 104 utilizing body fluid as the electrolyte. In such an instance, anode 104 may be of any conventional shape including, without limitation, a cylinder or a disc and cathode 102 may be part of the load. The load, which is connected to anode 104 and cathode 102, includes, without limitation, an implantable medical device. Exemplary implantable medical devices include, without limitation, pacemakers, monitors, or implantable cardioverter defibrillators (ICDs).

When the load is an ICD, the superior vena cava (SVC) electrode of a defibrillator lead acts as cathode 102. The SVC electrode may be any material meeting the requirements for the cathode described above including platinum. The SVC electrode may also have a coating including, without limitation, platinum black, iridium oxide ($IrO_2$), ruthenium oxide ($RuO_2$), or an $IrO_2/RuO_2$ mixture.

In one embodiment, the SVC electrode of a defibrillator lead is coated, such as with a platinum black coating, and is shared as the cathode electrode. A magnesium electrode is placed in the subcutaneous tissue of a pectoral cavity. The two electrodes are separated, but both are connected to the medical device through the lead.

Such bioelectric batteries reduce the size and number of components which need to be implanted.

Figure 4:
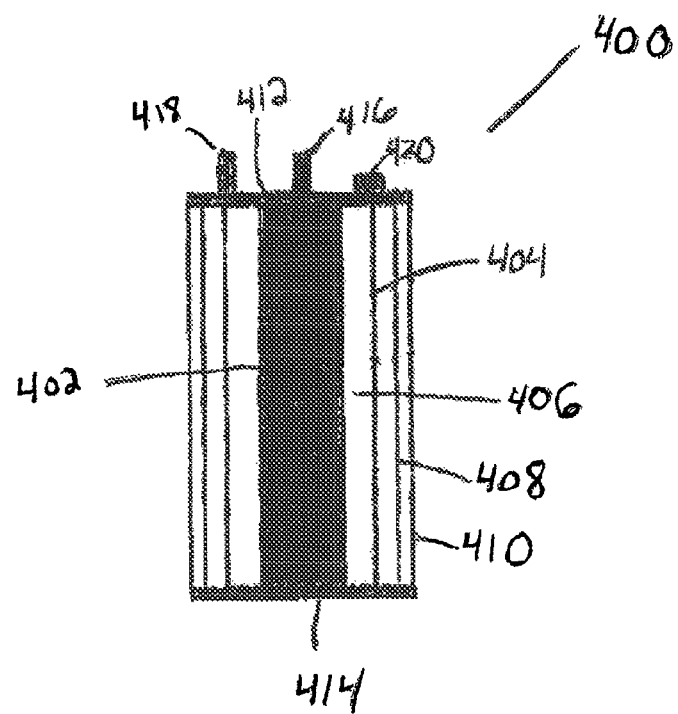
FIG. 4 is a cross-sectional view of an exemplary bioelectric battery according to a second embodiment.

A second embodiment of the bioelectric battery is generally shown at 400 in FIG. 4. Bioelectric battery 400 is an encapsulated battery having an anode electrode 402 surrounded by a cathode electrode 404 with an electrolyte 406 therebetween.

The materials for anode 402 and cathode 404 are chosen that do not exhibit toxicity to the body of the organism in which they are implanted. Anode 402 will be a reactive consumable metal that is consumed during the operation of the bioelectric battery and released into the body. Therefore it should be a material that is normally present in the body and of a size that when released into the body does not increase the levels of the material beyond a normally recommended level. The material for anode 402 should also exhibit good corrosion resistance. Anode corrosion, caused by substances in the body fluids corroding the anode material, shortens the life of the bioelectric battery. Anode material 104 should generate a high voltage with oxygen. The material for anode 402 may include, but is not limited to, magnesium alloys. Magnesium alloys include magnesium along with aluminum, zinc, manganese, silver, copper, nickel, zirconium and/or rare earth elements, such as neodymium, gadolinium, and yttrium. Such magnesium alloys include, without limitation, AZ61A supplied by Metal Mart International or AZ91E, EL21, or WE43 supplied by Magnesium Elektron. The material for cathode 404 is a non-consumable metal including, without limitation, platinum or titanium. Cathode 404 may be in the form of, including, without limitation, a foil or wire. Cathode 404 may have a coating that will act as a catalyst for its reaction by increasing the surface area of cathode 102 and thereby resulting in a faster reaction and increased voltage generation. The coating may include, without limitation, platinum black, iridium oxide ($IrO_2$), ruthenium oxide ($RuO_2$), or an $IrO_2/RuO_2$ mixture. The coating may be applied using conventional methods including, without limitation, electrochemical deposition, thermal decomposition or sputtering.

Electrolyte 406 is not body fluid and may be any other known conventional electrolyte that is less corrosive to the anode than body fluids in the form of a liquid or a gel. Examples include, but are not limited to, a gel or a solvent, e.g. isopropanol based solution containing a conductive component, such as sodium trifluoromethanesulfonate ($CF_3SO_3Na$) or sodium citrate dihydrate ($Na_3C_6H_5O_7.2H_2O$). There is no direct contact between cathode 404 and the body fluid, as the cathode is encapsulated with a permeable membrane 408 to prevent direct contact with the body fluid. Therefore, the oxygen must diffuse through permeable membrane 408 to reach cathode 404 and anode 402.

A permeable membrane 408 surrounds cathode 404. Permeable membrane 408 separates body fluids from cathode 404 and anode 402, thereby preventing corrosion of anode 402 from substances in the body fluids. Permeable membrane 408 is made from a porous polymeric material that allows oxygen in body fluids to diffuse through permeable membrane 408, but prevents other substances in the body fluid from passing through permeable membrane 408. Suitable materials for permeable membrane 408 include silicone and polytetrafluoroethylene (PTFE).

A mesh material 410 may surround permeable membrane 408. Mesh 410 provides strength to bioelectric battery 400, provides protection, and further reduces tissue encapsulation. Suitable materials for mesh 410 include, without limitation, stainless steel, titanium or other biocompatible material.

Bioelectric battery 400 also includes a top plate 412 and a bottom plate 414 joined to permeable membrane 408 to form an encapsulated bioelectric battery. Top plate 412 has a connection point 416 for connecting anode 402 to a load, a connection point 418 for connecting cathode 404 to a load, and an opening 420 for introducing electrolyte into battery 400. A load (not shown) is connected in parallel to anode 402 and cathode 404. Bioelectric battery 400 provides power to the load. The load includes, without limitation, an implantable medical device (not shown) and is connected in a similar fashion as illustrated in FIG. 3 for the bioelectric battery of the first embodiment. Exemplary implantable medical devices include, without limitation, pacemakers, monitors or implantable cardioverter defibrillators (ICDs). In the case of an ICD, bioelectric battery 400 provides power to the background operations.

In one embodiment, two electrodes are built in an encapsulated cell 400. A magnesium electrode 402 is placed in the center and a titanium foil electrode 404 is placed around the magnesium electrode 402. In one embodiment, electrode 402 acts as an anode material and electrode 404 acts as a cathode electrode. Electrode 404 may include a support substrate and electrode 404 is placed around electrode 402 such that an inside surface of the support substrate faces electrode 402. The support substrate may be a biocompatible, polymeric material and have openings along its length to allow electrolyte 406 to contact electrode 404. In one embodiment, electrode 404 may be a wire coiled around the support substrate. The titanium foil may be coated, such as with a platinum black, iridium oxide or ruthenium oxide coating. A porous polymer membrane is placed around the titanium foil cathode. Oxygen in the body fluid can pass through the permeable membrane into the cell. A stainless steel mesh is placed around the membrane. A conductive electrolyte that is less corrosive than the body fluid is filled in the cell. The anode corrosion problem is reduced, since the magnesium electrode is exposed to the selected electrolyte, instead of the body fluid. Additionally, since the cell is isolated, the electrodes do not touch the tissue, so there is no current passing through the surrounding tissue.

Bioelectric battery 400 is implanted in the body such that permeable membrane 408 is in direct contact with body fluids. Oxygen in the body fluids diffuses through permeable membrane 408 and into bioelectric battery 400. A plurality of bioelectric batteries 400 can also be connected in series.

Such bioelectric batteries minimize tissue encapsulation and/or anode corrosion.

Figure 5:
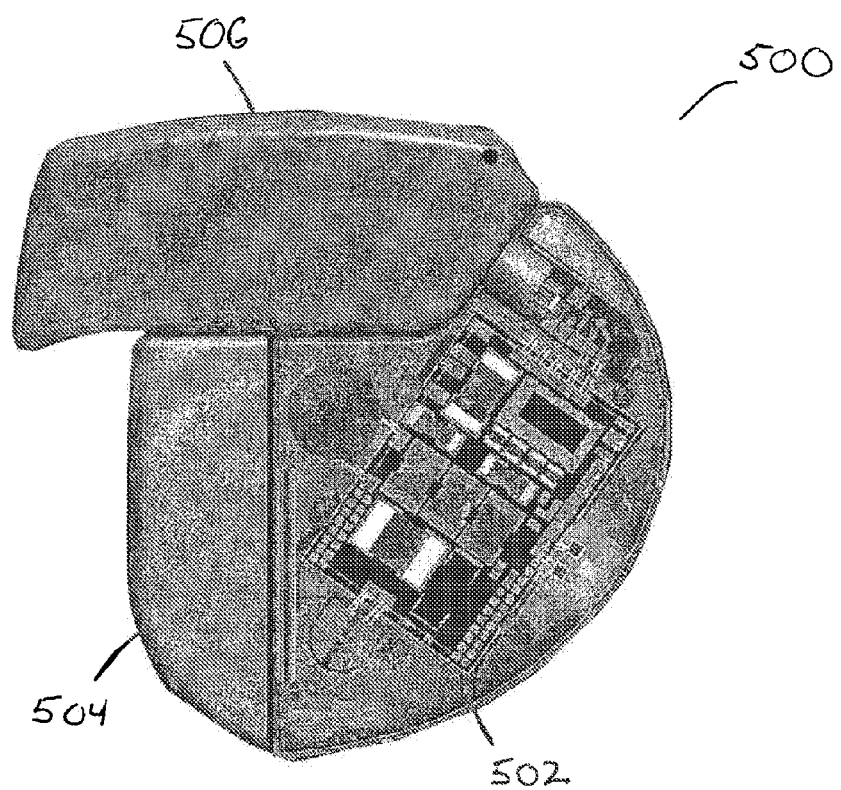
FIG. 5 is an exemplary view of an exemplary bioelectric battery according to a third embodiment.

In a third embodiment, as exemplary shown in FIG. 5, the bioelectric battery is formed as a single unit with a pacemaker 500 or other device wherein the housing acts as a cathode electrode. In this manner, the can 502 of the pacemaker 500 acts as the cathode electrode. The can 502 of pacemaker 500 is titanium or other material meeting the requirements for the cathode described above. Can 502 may have a coating including, without limitation, platinum black, iridium oxide ($IrO_2$), ruthenium oxide ($RuO_2$), or an $IrO_2/RuO_2$ mixture. The coating may be applied using conventional methods including, without limitation, electrochemical deposition, thermal decomposition or sputtering.

An anode electrode 504 is insulated from but integrated with the can 502 of pacemaker 500 as a single unit. The material for anode 504 should not exhibit toxicity to the body of the organism in which it is implanted and should generate a high voltage with the oxygen. Anode 504 will be a reactive consumable metal that is consumed during the operation of the bioelectric battery and released into the body. Therefore it should be a material that is normally present in the body and of a size that when released into the body does not increase the levels of the material beyond a normally recommended level. The material for anode 504 should also exhibit good corrosion resistance. The material for anode 504 may include, but is not limited to, magnesium alloys. Magnesium alloys include magnesium along with aluminum, zinc, manganese, silver, copper, nickel, zirconium and/or rare earth elements, such as neodymium, gadolinium, and yttrium. Such magnesium alloys include, without limitation, AZ61A supplied by Metal Mart International or AZ91E, EL21, or WE43 supplied by Magnesium Elektron.

Anode 504 may be attached to pacemaker 500 through an insulating adhesive such as epoxy. Alternatively, anode 504 may be detached from pacemaker 500, however the distance apart is optimized to reduce impedance. A conventional header 506 is attached to the can 502 of pacemaker 500 in order to connect to pacing leads.

The electrolyte for the bioelectric battery wherein can 502 acts as a cathode may be a body fluid including, without limitation, blood. The body fluid directly contacts can 502 and anode 504, such that oxygen dissolved in the body fluid is absorbed onto a surface of can 102.

The volume of anode 504 is smaller than a traditional lithium battery utilized to power a pacemaker, so the size of the pacemaker/battery combination is smaller than a conventional pacemaker having a traditional lithium battery.

While various embodiments of the present invention have been described above, it should be understood that they have been presented by way of example only, and not limitation. It will be apparent to persons skilled in the relevant art that various charges in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An implantable power supply comprising:
a bioelectric battery for implantation into a living body as a single unit, said battery including:
an anode electrode;
a cathode electrode wire, wherein said cathode electrode wire is coiled around said anode electrode; and
an insulating member separating said anode electrode from said cathode electrode, all within said single unit, wherein a surface of said cathode electrode is configured to absorb oxygen when oxygen dissolved in body fluid directly contacts the cathode electrode and wherein the anode electrode is configured to react with the oxygen when it is absorbed on the surface of the cathode electrode.

2. The battery of claim 1 wherein said anode electrode is at least partially inserted into and surrounded by said insulating material and wherein said cathode wire at least partially surrounds said insulating member.

3. The battery of claim 1 and further including an oxygen permeable membrane surrounding at least said cathode electrode.

4. The battery of claim 1 wherein said anode electrode and cathode electrode are both exposed directly to a body fluid.

5. The battery of claim 1 wherein said anode electrode comprises a magnesium alloy.

6. The battery of claim 1 wherein said anode electrode is selected from the group consisting of pure magnesium, pure zinc, pure aluminum, a zinc alloy and an aluminum alloy.

7. The battery of claim 3 wherein said membrane has a first open end and a second open end such that body fluid may flow through said first and second open ends of said membrane to contact said cathode electrode and said anode electrode.

8. The battery of claim 1 wherein said cathode electrode comprises a cathode electrode material and wherein said cathode electrode material is titanium.

9. The battery of claim 1 wherein said cathode electrode comprises a cathode electrode material and wherein said cathode electrode material is titanium having an iridium oxide coating.

10. The battery of claim 1 wherein said cathode electrode has a coating selected from the group consisting of platinum black, iridium oxide, ruthenium oxide and mixtures thereof.

11. The battery of claim 1, further including a lead extending from said single unit and coupling said anode electrode and said cathode electrode to a load.

12. A bioelectric battery for implantation into a living body as a single unit comprising:
an anode electrode;
a cathode electrode foil, wherein said cathode electrode foil surrounds said anode electrode; and
an insulating member separating said anode electrode from said cathode electrode, wherein a surface of said cathode electrode is configured to absorb oxygen when oxygen dissolved in body fluid directly contacts the cathode electrode and wherein the anode electrode is configured to react with the oxygen when it is absorbed on the surface of the cathode electrode.

13. The battery of claim 12 wherein said anode electrode is at least partially inserted into and surrounded by said insulating material and wherein said cathode electrode foil at least partially surrounds said insulating member.

14. The battery of claim 12 and further including an oxygen permeable membrane surrounding at least said cathode electrode.

15. The battery of claim 12 wherein said anode electrode and cathode electrode are both exposed directly to a body fluid.

16. The battery of claim 12 wherein said anode electrode comprises a magnesium alloy.

17. The battery of claim 12 wherein said anode electrode is selected from the group consisting of pure magnesium, pure zinc, pure aluminum, a zinc alloy and an aluminum alloy.

18. The battery of claim 14 wherein said membrane has a first open end and a second open end such that body fluid may flow through said first and second open ends of said membrane to contact said cathode electrode and said anode electrode.

19. The battery of claim 12 wherein said cathode electrode comprises a cathode electrode material and wherein said cathode electrode material is titanium.

20. The battery of claim 12 wherein said cathode electrode comprises a cathode electrode material and wherein said cathode electrode material is titanium having an iridium oxide coating.

21. The battery of claim 12 wherein said cathode electrode has a coating selected from the group consisting of platinum black, iridium oxide, ruthenium oxide and mixtures thereof.

22. The battery of claim 12, further including a lead extending from said single unit and coupling said anode electrode and said cathode electrode to a load.

23. An implantable power supply comprising:
a bioelectric battery for implantation into a living body as a single unit, said battery including:
an anode electrode;
a cathode electrode, wherein said cathode electrode is wrapped around said anode electrode; and
an insulating member separating said anode electrode from said cathode electrode, all within said single unit, wherein a surface of said cathode electrode is configured to absorb oxygen when oxygen dissolved in body fluid directly contacts the cathode electrode and wherein the anode electrode is configured to react with the oxygen when it is absorbed on the surface of the cathode electrode.

* * * * *